United States Patent [19]

Naik et al.

[11] Patent Number: 4,772,605

[45] Date of Patent: Sep. 20, 1988

[54] BASIC FORMULATIONS OF QUINOLONECARBOXYLIC ACIDS

[75] Inventors: Arundev H. Naik, Leverkusen; Gerhard Schlüter, Wuppertal; Herbert Voege, Leverkusen; Klaus Grohe, Odenthal, all of Fed. Rep. of Germany

[73] Assignee: Bayer Aktiengesellschaft, Leverkusen, Fed. Rep. of Germany

[21] Appl. No.: 97,017

[22] Filed: Sep. 14, 1987

Related U.S. Application Data

[63] Continuation of Ser. No. 811,915, Dec. 20, 1985, abandoned.

[30] Foreign Application Priority Data

Jan. 5, 1985 [DE] Fed. Rep. of Germany ....... 3500243
May 17, 1985 [DE] Fed. Rep. of Germany ....... 3517709

[51] Int. Cl.$^4$ .................. A61K 31/495; C07D 53/126
[52] U.S. Cl. .................................. 514/254; 544/101; 544/362; 544/363
[58] Field of Search ...................... 544/361, 362, 363; 514/254

[56] References Cited

U.S. PATENT DOCUMENTS 4,352,803 10/1982 Matsumoto et al. .

FOREIGN PATENT DOCUMENTS 0047005  3/1982  European Pat. Off. .
0067666  12/1982  European Pat. Off. .
0098577  1/1984  European Pat. Off. .
0142426  5/1985  European Pat. Off. .
2914258  10/1979  Fed. Rep. of Germany .
2940810  4/1980  Fed. Rep. of Germany .
3037103  5/1981  Fed. Rep. of Germany .
3033157  4/1982  Fed. Rep. of Germany .
3142854  5/1983  Fed. Rep. of Germany .

Primary Examiner—Donald G. Daus
Assistant Examiner—Cecilia Shen
Attorney, Agent, or Firm—Sprung Horn Kramer & Woods

[57] ABSTRACT

Improvement in the parenteral administration of a carboxylic acid of the formula

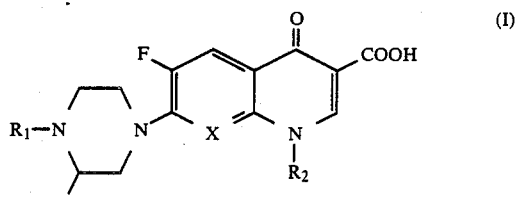

or

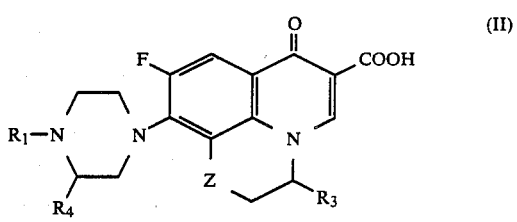

in which
X is N, C—H or C—F,
Z is O or $Ch_2$,
$R_1$ is hydrogen, methyl, ethyl or β-hydroxyethyl,
$R_2$ is cyclopropyl, 2-fluoroethyl or ethyl,
$R_3$ is hydrogen or methyl, and
$R_4$ is H or methyl, is achieved through the administration of the basic salt of the acid (I, II). Surprisingly the basic salts are suitable and stable.

3 Claims, No Drawings

BASIC FORMULATIONS OF QUINOLONECARBOXYLIC ACIDS

This is a continuation of application Ser. No. 811,915, filed Dec. 20, 1985, now abandoned.

The invention relates to aqueous basic formulations of quinolonecarboxylic acids, if appropriate in the form of concentrates, and their use for the preparation of medicaments which are suitable for injection, infusion or oral administration.

Quinolonecarboxylic acids and their analogues are known. They have a good bactericidal action (compare EP-OS (European Published Specification) No. 67,666, DE-OS (German Published Specification) No. 2,914,258; DE-OS (German Published Specification) No. 2,940,810; DE-OS (German Published Specification) Nos. 3,142,854; 3,033,157; EP-OS (European Published Specification) No. 47,005 and DE-OS (German Published Specification) No. 3,037,103).

However, the active compounds are water-insoluble or only sparingly soluble in water and therefore cannot be used, or can be used only with difficulty, in injection or infusion solutions or solutions for oral administration. Since the active compounds contain both basic and acidic groups, the formation of salts has already been described in the abovementioned literature references. Salts with acids are indeed water-soluble. However, for example, hydrochlorides tend to precipitate during storage. In addition, solutions of acid salts cannot be diluted with electrolytic solutions, such as, for example, physiological saline solution, since precipitation of the active compounds thereby also occurs.

Aqueous solutions of salts of quinolonecarboxylic acids with acids also exhibit discoloration on storage, which indicates a poor photostability of these salts.

The invention relates to aqueous basic formulations of quinolonecarboxylic acids of the general formulae I or II

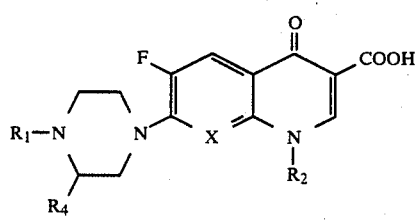

(I)

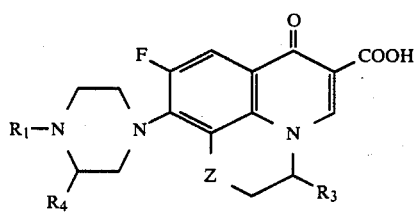

(II)

in which
X denotes N, C—H or C—F,
Z denotes O or CH$_2$,
R$_1$ denotes hydrogen, methyl, ethyl or β-hydroxyethyl,
R$_2$ denotes cyclopropyl, 2-fluoroethyl or ethyl,
R$_3$ denotes hydrogen or methyl and
R$_4$ denotes H or methyl,
which are characterized in that they contain the compounds of the formulae I or II in the form of their salts with bases, if appropriate in the presence of an excess of base, and if appropriate in the presence of further auxiliaries.

Aqueous basic formulations according to the present invention are suitable as injection and infusion solutions, but also as concentrates which can be diluted to the use concentration before injection or infusion. They are also suitable, either directly or diluted, for oral administration.

Oral administration includes administration via drinking water. They can be employed both in human medicine and in veterinary medicine for combating bacterial infections.

It was surprising that, in contrast to the acid formulations, no discoloration or precipitation occurs in the basic formulations according to the invention during storage of the formulations.

The basic formulations according to the invention also prove to be just as suitable for injection and infusion as the formulation which has been prepared from salts of the compounds of the formula I with acids. According to the information in EP-OS (European Published Specification) 67,666, page 14, lines 16-17, this was not to be expected. This literature reference states that, because of their pH value, the sodium and choline salts of quinolonecarboxylic acids are unsuitable for parenteral formulations. Salts of quinolonecarboxylic acids with galacturonic, asparagine, gluconic or glutamic acid are then given as a solution to the problem. The particular suitability of basic salts for the preparation of parenteral formulations was not recognized.

Compounds of the formulae I or II which are preferably used are those in which
X represents N, C—H or C—F,
Z denotes oxygen,
R$_1$ represents hydrogen, methyl or ethyl,
R$_2$ denotes ethyl, cyclopropyl or 2-fluoroethyl,
R$_3$ represents hydrogen or methyl and
R$_4$ represents hydrogen or methyl.

Compounds of the formulae I or II which are particularly preferred are those in which
X represents N, C—H or C—F,
Z denotes oxygen,
R$_1$ denotes hydrogen, methyl or ethyl,
R$_2$ denotes cyclopropyl,
R$_3$ denotes methyl and
R$_4$ denotes hydrogen and/or methyl.

Compounds which may be mentioned in particular are 1-cyclopropyl-6-fluoro-1,4-dihydro-4-oxo-7-(1-piperazinyl or 4-ethyl-1-piperazinyl-)quinoline-3-carboxylic acid, 1-ethyl-6-fluoro-1,4-dihydro-4-oxo-7-(1-piperazinyl)-quinoline-3-carboxylic acid, 1-ethyl-6-fluoro-1,4-dihydro-4-oxo-7-(1-piperazinyl)-1,8-naphthyridine-3-carboxylic acid and 9-fluoro-3-methyl-10-(4-methyl-1-piperazinyl)-7-oxo-2,3-dihydro-7,4-pyrido[1,2,3-de]1,4-benzoxazine-6-carboxylic acid.

As already mentioned, the compounds of the formulae I or II are present in the formulations according to the invention in the form of their salts with bases. Bases include inorganic and organic bases which form physiologically acceptable salts in the use concentrations. Bases which may be mentioned are the inorganic bases NaOH, KOH, Ca(OH)$_2$ and ammonia. Organic bases which may be mentioned are amines, such as mono-, di- and trialkylamines, substituted amines, such as ethanolamine, cyclic amines, such as morpholine and piperazine, and basic aminoacids, such as arginine, lysine, choline and N-methyl-glucamine.

The following bases are preferred: NaOH, KOH, ethanolamine, lysine, N-methylglucamine and arginine.

The following bases are particularly preferred: NaOH, KOH and arginine.

Water can be used as a solvent for the formulations according to the invention. If appropriate, mixtures of water with other solvents can also be used. Solvents include: alcohols, such as monohydric or polyhydric primary, secondary or tertiary alkanols, such as, for example, ethanol, butanol, benzyl alcohol, glycol, glycerol and propylene glycol, and N-methylpyrrolidone.

The following alcohols are preferred: ethanol, butanol and glycerol.

The following alcohols are particularly preferred: butanol and benzyl alcohol.

The concentration of the solvents in the formulations according to the invention is 1–30%, preferably between 1 and 10% and especially preferably between 1 and 3%.

Customary auxiliaries can be added to the formulations according to the invention. Possible auxiliaries are non-toxic pharmaceutical substances, such as diluents, absorption accelerators, absorption inhibitors, crystallization retarders, complexing agents, antioxidants, preservatives and protonizing agents.

Auxiliaries which may be mentioned as particularly preferred are: preservatives, for example p-hydroxybenzoic acid esters or phenols, antioxidants, for example sodium meta-bis-sulphite or sodium sulphite, complexing agents, such as sodium salts of ethylenediaminetetraacetic acid, and crystallization retarders, such as polyvinylpyrrolidone.

The concentration of the auxiliaries in the formulations according to the invention is 0.1–10%, preferably 1–2%.

The basic salts of the compounds of the formula I are present in the formulations according to the invention in concentrations of 0.1–30%, preferably, depending on the nature of the application, between 0.5 and 10% or 0.2 and 2% or 10 and 30%. Solutions containing 0.5–10% are particularly preferred.

In addition to the salts, the formulations according to the invention can contain bases in more than the equimolar amounts. The bases which have also been used to form the salts are preferred here. The excess of base is between 0.01 and 100 me/l, preferably between 0.1 and 50 me/l and particularly preferably between 0.5 and 30 me/l (me=milliequivalents in grams/liter).

The pH value of the formulation according to the invention is between 8 and 12.5, preferably between 9 and 11.

To prepare the formulations according to the invention, salts of the compounds of the formulae I or II or hydrates thereof can be used as starting substances. The desired amount of the salts is dissolved in water and, if appropriate, further base is added.

However, it is also possible to prepare the salts directly in the solution, and in particular by adding the amounts of base required for salt formation to the compounds of the formulae I or II.

Preferably, the aqueous basic formulations of the carboxylic acids of the formulae I or II are prepared by a procedure in which (a) the active compound is introduced into water, if appropriate together with a formulation auxiliary, an inorganic or organic base is slowly stirred in until a pH value of 8 to 12.5 has been established and, after the active compound has been dissolved, a further amount of water is added, if appropriate, until the desired concentration is reached, or (b) the active compound and, if appropriate, formulation auxiliaries are suspended in water, an inorganic or organic base is added, with stirring, until the active compound has dissolved, stirring is continued until a clear gel which is free from lumps has formed and, if appropriate, the gel is then diluted with water to the desired concentration, or (c) the compounds of the formulae I or II are dissolved in water in the form of their salts with bases and, if appropriate, the pH value is brought to 8 to 12.5 with an excess of a base.

Both ready-to-use solutions of the active substance, bottled in suitable containers, for example in ampules or injection or infusion bottles, and also precursors suitable for the preparation of such for solutions, for example concentrates or dry ampules can be prepared in this manner.

The solutions according to the invention as well as the compounds of the formulae I or II on which they are based are intended for use as medicaments for combating bacterial infections in the human or veterinary field. Possible uses are injections and infusions, and also oral solutions or mastitis instillates. The dosages correspond to those which are known for the known compounds of the formula I.

EXAMPLES

Active compounds:

1-Cyclopropyl-6-fluoro-1,4-dihydro-4-oxo-7-(4-ethyl-1-piperazinyl-)quinoline-3-carboxylic acid (I) and 1-cyclopropyl-6-fluoro-1,4-dihydro-4-oxo-7-(1-piperazinyl)-quinoline-3-carboxylic acid (II) are used as the active compounds in the following examples.

General Instructions I:

The active compound is added to some of the stated amount of water and the auxiliaries, and the base is slowly stirred in until the stated pH value has been established (checked with a glass electrode). During the addition of the base, the active compound dissolves. After the active compound has dissolved, the remainder of the water is added and the solution is subjected to sterile filtration.

Example 1

| | |
|---|---|
| Active compound (I) | 0.5 g |
| Benzyl alcohol | 1.5 g |
| Potassium hydroxide to pH 11 | 0.082 g |
| Water for injection purposes to | 100 ml |

Example 2

| | |
|---|---|
| Active compound II | 30.00 g |
| Potassium hydroxide to pH 11 about | 5.10 g |
| Benzyl alcohol | 1.5 g |
| Water for injection purposes to | 100 ml |

Example 3

| | |
|---|---|
| Active compound I | 10.00 g |

-continued

| | |
|---|---|
| Sodium hydroxide solution 1N to pH 11 about | 29.00 g |
| n-Butanol | 3.00 g |
| Water for injection purposes to | 100 ml |

Example 4

| | |
|---|---|
| Active compound II | 5.00 g |
| n-Butanol | 3.00 g |
| Polyvinylpyrrolidone 25 | 10.00 g |
| Potassium hydroxide to pH 11 about | 0.86 g |
| Water for injection purposes to | 100 ml |

Example 5

| | |
|---|---|
| Active compound I | 5.00 g |
| N—Methylglucamine | 6.50 g |
| Water for injection purposes to | 100 ml |
| pH of the solution: 10.5. | |

Example 6

| | |
|---|---|
| Active compound I | 10.00 g |
| L Arginine Base | 20.00 g |
| Benzyl alcohol | 1.00 g |
| n-Butanol | 3.00 g |
| Water for injection purposes to | 100 ml |

Example 7

| | |
|---|---|
| Active compound | 0.50 g |
| Potassium hydroxide | 0.56 g |
| Glycine | 0.75 g |
| Potassium chloride | 0.75 g |
| Benzyl alcohol | 1.00 g |
| Water for injection purposes to | 100 ml |

General Instructions II:

The active compound and the auxiliaries are suspended in most of the water. The alkali is carefully added, with stirring, until the active compound has dissolved. Stirring is continued until a clear, mobile gel with no lumps has formed.

Example 8

| | |
|---|---|
| Active compound I | 2.500 g |
| Benzyl alcohol | 1.400 g |
| Methyl-hydroxypropyl-cellulose | 3.500 g |
| Potassium hydroxide to pH 11 about | 0.397 g |
| demineralized water | 93.703 g |
| 100 ml ≙ | 101.500 g |

Example 9

| | |
|---|---|
| Active Compound II | 2.00 g |
| Na salt of polyacrylic acid | 0.62 g |
| Sodium hydroxide solution 1N about | 6.20 g |
| Benzyl alcohol | 1.00 g |
| demineralized water | 91.28 g |
| 100 ml ≙ | 100.70 g |

Example 10

| | |
|---|---|
| Active compound I | 20.00 g |
| Benzyl alcohol | 1.00 g |
| 10% strength potassium hydroxide solution about | 31.70 g |
| Hydroxypropylmethyl cellulose phthalate | 2.00 g |
| demineralized water | 52.80 g |
| 100 ml ≙ | 107.50 g |

It is understood that the specification and examples are illustrative but not limitative of the present invention and that other embodiments within the spirit and scope of the invention will suggest themselves to those skilled in the art.

We claim:

1. An aqueous solution of pH 8 to 12.5 of a basic salt of a carboxylic acid of the formula

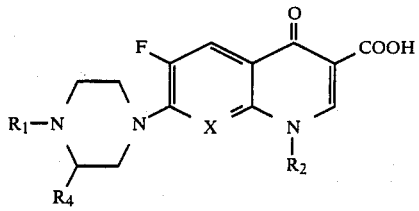

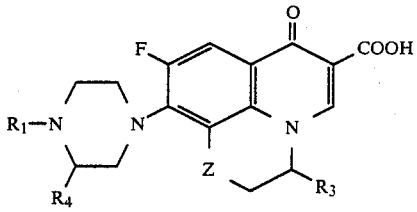

in which
X is N, C—H or C—F,
$R_1$ is hydrogen, methyl, ethyl or β-hydroxyethyl,
$R_2$ is cyclopropyl, 2-fluoroethyl or ethyl, and
$R_4$ is H or methyl,
and 0.01 to 100 milliequivalents per liter of an excess of a base selected from the group consisting of sodium hydroxide, potassium hydroxide and arginine.

2. A solution according to claim 1, wherein the carboxylic acid is 1-cyclopropyl-6-fluoro-1,4-dihydro-4-oxo-7-(1-piperazinyl)-3-quinolinecarboxylic acid.

3. A solution according to claim 1, wherein the carboxylic acid is 1-cyclopropyl-7-(4-ethyl-1-piperazinyl)-6-fluoro-1,4-dihydro-4-oxo-3-quinolinecarboxylic acid.

* * * * *

UNITED STATES PATENT AND TRADEMARK OFFICE
CERTIFICATE OF CORRECTION

PATENT NO. : 4,772,605

DATED : September 20, 1988

INVENTOR(S) : Arundev H. Naik, et al

It is certified that error appears in the above-identified patent and that said Letters Patent is hereby corrected as shown below:

Col. 3, line 31   Delete "meta-bis-" and substitute --meta-bi- --

Col. 6, lines 40-48   Delete second formula

Signed and Sealed this

Twentieth Day of June, 1989

Attest:

DONALD J. QUIGG

Attesting Officer

Commissioner of Patents and Trademarks